United States Patent [19]

Hunter

[11] Patent Number: 4,840,906

[45] Date of Patent: Jun. 20, 1989

[54] PLANT GENERATION METHOD

[75] Inventor: Clifford P. Hunter, Sittingbourne, England

[73] Assignee: Shell Oil Company, Houston, Tex.

[21] Appl. No.: 49,360

[22] Filed: May 14, 1987

[30] Foreign Application Priority Data

May 15, 1986 [GB] United Kingdom ............... 8611818

[51] Int. Cl.$^4$ .............................................. C12N 5/00
[52] U.S. Cl. ........................... 435/240.49; 435/240.5; 435/240.54
[58] Field of Search ........... 435/240.5, 240.54, 240.49; 47/58

[56] References Cited

PUBLICATIONS

Grant et al., 1987, pp. 409, 463 In: Grant & Hackh's Chemical Dictionary, 5th Edition, (Grant et al., eds.), McGraw-Hill: New York.
Kirk-Othmer, 1964, Encyclopedia of Chemical Technology (John Wiley and Sons), p. 133.
Gonzalez-Medina et al., 1978, Euphytica 27(2): 553-559.
Raquin, Z. Pflanzenphysial Bd., 111, S, 453-457 (1983).
Snape, J. W., Induced Variability in Plant Breeding, PUDOC, Wageningen (ISBN 90 220 07960), 1982, pp. 52-58.
Huang et al., Ann. Bot., 49, pp. 77-88 (1982).
Hunter, Plant Cell Reports, 1985, 4, pp. 267-268.

Primary Examiner—Charles F. Warren
Assistant Examiner—David T. Fox

[57] ABSTRACT

The invention provides a method of generating barley plants comprising culturing barley microspores on a sugar-containing medium and harvesting green plantlets from the medium characterized in that the sugar in the sugar-containing medium is at least one sugar selected from sucrose; glucose; and oligosaccharides and polysaccharides containing at least two glucose residues; wherein the concentration of sucrose and glucose in the medium is not greater than 0.03 mol/l; and a method of generating barley seed which comprises the additional steps of cultivating green plantlets and deriving seed from resulting mature plants.

8 Claims, No Drawings

PLANT GENERATION METHOD

This invention relates to a method of generating plants, more particularly barley plants, and to a method of generating barley seed.

Microspore culture is the technique of growing plants from immature pollen cells. The technique is of particular value for the breeding of new plant varieties. It also enables the application of a wide range of genetic manipulation techniques, including transformation to incorporate foreign or modified genes and protoplast fusion to allow hybridisation between related plant species.

Pollen cells are haploid (i.e. they contain only a single set of unpaired chromosomes). Plants obtained from pollen cells are also normally haploid; as such, they are of interest to geneticists, but are not directly useful in plant breeding because they are sterile. The chromosome complement can, however, be doubled by colchicine treatment, or (as is the case with barley) this may occur spontaneously in culture. The resulting plants are termed doubled haploids; they contain two identical copies of each chromosome and are therefore true breeding. These true breeding doubled haploids allow the development of homozygous lines from heterozygous parents in a single generation.

In a conventional breeding programme for an inbred crop such as wheat or barley it takes eight to ten generations to produce a true breeding variety. The production of doubled haploids at an early generation (e.g. from an $F_1$ hybrid) will reduce the time required to produce useful new varieties. The potential time saving depends on the crop, being greater in biennial than in annual species, and in winter than in spring varieties, although those skilled in the art will appreciate that a number of generations are still required for disease screening, yield trials and bulking-up of seed.

Also important is the fact that the genotypes of doubled haploid lines are fixed and stable. Plants may be selected in the knowledge that they will breed true, by contrast with conventional breeding, where selections are made on segregating populations. The use of doubled haploids may thus help to improve the overall efficiency of selection in a breeding programme.

Microspore culture is only one of several ways of producing doubled haploids. In all other methods plants are derived from the egg cell through one of a number of mechanisms, which are fundamentally of two kinds: either the egg may be stimulated to grow without fertilisation, or one genome may be eliminated following a wide cross. A well known example of the latter is the production of barley haploids following pollination by a wild barley grass, *Hordeum bulbosum* (the so-called *H. bulbosum* technique).

The use of doubled Haploids in breeding programmes has been reviewed by J.W. Snape, Induced Variability in Plant Breeding, PUDOC, Wageningen (ISBN 90 220 07960) (1982) pages 52 to 58. The major limitation which has prevented their large scale use in barley breeding has been the very low efficiency, in terms of the numbers of plants produced per man year of effort. Presently available techniques are not generally considered to compete with conventional pedigree breeding. Nevertheless the potential of doubled haploids has been demonstrated by the release of the variety Mingo in Canada which was produced by the so-called *H.bulbosum* technique, although this technique has the disadvantage that the generally accepted rate of production of doubled haploid plants by a skilled full-time operator is only about 1500 per year.

Microspore culture has an intrinsic potential advantage over techniques involving egg cells, because plants produce far more pollen cells than egg cells. The potential of the culture technique, however, will not be realised with the major crop species unless efficiency can be substantially improved to allow the production of very large numbers of plants for an acceptable level of effort.

Microspores are found in the anthers of plants, and the efficiency of culture is usually expressed as the number of green plants produced per 100 anthers used. Typical published yields for the most responsive varieties of barley (sucrose being employed as carbon source) are of the order of 2 to 5 green plants per 100 anthers (e.g. Huang and Sunderland, Ann. Bot. 49, 77-78, 1982).

The two most widely used sugars for the culture of plant tissues are sucrose and glucose, although lactose, maltose, fructose and galactose have been used successfully for rice calluses; tobacco plantlets have been obtained using fructose; and maltose, lactose and fructose have been used successfully in anther culture of Petunia (Raquin, Z. Pflanzenphysiol Bd. 111.S.453-457 (1983)).

It has now surprisingly been found that certain modifications in relation to the sugar component in the culture medium enable significantly enhanced efficiency to be achieved in barley microspore culture.

Accordingly the present invention provides a method of generating barley plants comprising culturing barley microspores on a sugar-containing medium and harvesting green plantlets from the medium characterised in that the sugar in the sugar-containing medium is at least one sugar selected from sucrose; glucose; and oligosaccharides and polysaccharides containing at least two glucose residues; wherein the concentration of sucrose and glucose in the medium is not greater than 0.03 mol/l.

The oligosaccharides and polysaccharides must contain at least two glucose residues, and may contain exclusively glucose residues. Preferred oligosaccharides are dissaccharides and trisaccharides. Disaccharides containing two glucose residues comprise maltose, trehalose, cellobiose and gentiobiose. Maltose, trehalose and cellobiose have been found to be particularly effective. Suitable trisaccharides include maltotriose and melezitose. Suitable polysaccharides are the various dextrins.

When the sugar is sucrose or glucose, the concentration of sucrose or glucose in the medium is preferably at least 0.0025 mol/l, and is preferably not greater than 0.015, especially 0.01 mol/l. It may be necessary to effect replenishment of the medium to maintain the sucrose or glucose levels and avoid deletion. The use of glucose is preferred.

The oligosaccharides may conveniently be employed at concentrations at which sucrose has been employed in prior art media (see e.g. Huang and Sunderland, Ann. Bot. 49, 77-88, 1982, Foroughi-Wehr et al, Z. Pflanzenzuchtg. 77, 198-204 (1976)). Concentrations in the range 0.05 to 0.35, preferably 0.05 to 0.2 mol/l, have been found to be very effective. At such concentrations, replenishment of the medium should be unnecessary. Polysaccharides may for example be used at concentrations in the range 2 to 12, preferably 2 to 8, percentage w/v (grams per 100ml).

If desired, one or more sugar alcohols, such as mannitol and sorbitol, may additionally be present in the medium.

The microspores cultured may be present in intact or damaged barley anthers, or they may be isolated from the anthers. The term microspore should be understood to include all stages of development from tetrad through to immature pollen grains. In a preferred embodiment of the process according to the invention, anthers are cultured directly.

After harvesting, the green plantlets may if desired be transferred to another culture medium prior to growing of rooted plantlets in soil for seed production.

The invention further provides a method of generating barley seed comprising generating barley plants by the above method of the invention, cultivating green plantlets and deriving seed from resulting mature plants.

The seem may be derived (in known manner) by harvesting it directly from the resulting mature plants or by replanting such harvested seed and obtaining seed from plants one or more generations remote from the original green plantlets.

The invention will be further understood from the following Examples, in which percentages are w/v (grams/100ml) unless otherwise specifically stated and the symbol "M" represents mol/1. In the Examples the following general procedure was employed.

Barley plants were grown in controlled environment cabinets at a constant 12° C. under a mixture of fluorescent and tungsten lighting for 16 hours/day (giving 350 $\mu Em^{-2}s^{-1}$ of photosynthetically active radiation) at 60-80% relative humidity. Tillers were harvested soon after emergence of the flag leaf ligule. Spikes were dissected out under sterile conditions after surface sterilisation of tillers with ethanol. The stage of anther development was determined on anthers taken from a central floret. The anthers were squashed gently in acetocarmine and examined microscopically. Only those spikes with anthers with microspores at the mid-uninucleate stage (see Huang and Sunderland, Ann. Bot. 49, 77-88, 1982) were used subsequently. Each selected spike was placed in one compartment of a two compartment Petri dish, with 1ml of sterile water in the other compartment to maintain humidity. The spikes were subjected to cold pretreatment by transferring the Petri dishes to a cold room at 4° C. for 28 days. At the end of this time the viability of microspores was assessed. Anthers from a second central floret were stained as above and examined microscopically. If the count revealed that 40% or more of the pollen had a nucleus or nuclei of normal appearance, the anthers from that spike were cultured.

Anthers were cultured in 5cm Petri dishes containing 10ml of the callus induction medium of Foroughi-Wehr et al, Z. Pflanzenzuchtg. 77, 198-204 (1976), except for substitution of sugar in place of the sucrose as hereinafter described. Except wehre otherwise stated, the medium was solidified with 0.8% Sea Plaque agarose (ex Miles Laboratories Ltd). Cultures were incubated in the dark at 25° C. for 28 days, then transferred to continuous light. Plantlets larger than 5mm were harvested at weekly intervals from 5 weeks after initiation of culture and grown on in Murashige and Skoog's medium (Murashige and Skoog, Physiologia Pl., Vol. 15, 1962, 473-97), without hormones, containing 2% sucrose and solidified with 0.6% Difco Bacto agar (ex Difco).

When rooted, plantlets could be established in soil and grown on to produce seed.

EXAMPLE 1

A comparison was made of plant production from anthers of the barley cultivar Sabarlis, cultured on sucrose or on maltose, in each case at 0.175 M (mol/l). The experiment was replicated ten times. For each replicate a total of 48 anthers were taken from central regions of two pretreated spikes and assigned randomly to the two media such that each plate received 24 anthers. Anthers were placed on-edge on the culture medium as described by Hunter (Plant Cell Reports, 4,267, 1985). Culture on maltose yielded 121.6 green plantlets per 100 anthers cultured, whereas culture on sucrose yielded only 12.5 green plantlets per 100 anthers cultured.

EXAMPLE 2

Example 1 was repeated using the barley variety Igri. For each replicate, anthers from one spike were randomly assigned to media containing 0.175 M sucrose or maltose. Each dish received 24 anthers and the experiment was replicated three times. Culture on maltose yielded 450 green plantlets per 100 anthers cultured, whereas the yield on sucrose was 78 green plantlets per 100 anthers cultured. Thus the maltose containing medium was nearly six times better than the sucrose medium. This result clearly demonstrates that the method of the invention is not specific to one variety of barley.

EXAMPLES 3 to 5

A comparison was made of plant production from anthers cultured on eight different sugars. Anthers of the barley cultivar Sabarlis were cultured both on edge and flat on the culture medium (see Hunter, Plant Cell Reports, (1985) 4: 267-268) because it had previously been observed that if anthers fell into the flat position plants developed well on maltose but poorly on sucrose medium.

The experiment was replicated five times. For each replicate a total of 54 anthers from each of 9 spikes were randomly assigned to the 18 treatments such that each dish received 27 anthers. Results obtained are shown in Table I following:

TABLE I

| | Sugar | Concentration (M) | Green plantlets per 100 anthers cultured | |
|---|---|---|---|---|
| | | | Anthers flat | Anthers on edge |
| Example | | | | |
| 3 | maltose | 0.175 | 65.8 | 78.0 |
| 4 | trehalose | 0.175 | 31.9 | 55.0 |
| 5 | cellobiose | 0.175 | 73.8 | 127.7 |
| Comparative | | | | |
| A | sucrose | 0.175 | 5.4 | 22.1 |
| B | glucose | 0.175 | 2.1 | 7.5 |
| C | glucose | 0.35 | 0.4 | 2.1 |
| D | fructose | 0.175 | 0.4 | 0.0 |
| E | lactose | 0.175 | 0.0 | 0.0 |
| F | raffinose | 0.175 | 10.6 | 22.6 |

The results demonstrate the superiority of maltose, trehalose and cellobiose over sucrose for plant production, regardless of anther orientation. Lactose, fructose and glucose were very poor substrates for anther culture at the concentrations tested.

EXAMPLES 6 to 9

The effect of mixtures of sugars, and addition of sugar alcohols, on anther culture was investigated. Anthers of the barley cultivar Igri were cultured flat on the culture medium.

The experiment was replicated three times. For each replicate, 54 anthers from each of 3 spikes were randomly assigned to the 9 treatments such that each dish received 18 anthers. Results obtained are shown in Table II following:

TABLE II

| Example | Maltose concentration (M) | Other sugar/ sugar alcohol (OS/SA) | Concentration of OS/SA (M) | Green plantlets per 100 anthers cultured |
|---|---|---|---|---|
| 6 | 0.175 | — | — | 213 |
| 7 | 0.117 | — | — | 172 |
| 8 | 0.117 | mannitol | 0.058 | 165 |
| 9 | 0.117 | sorbitol | 0.058 | 170 |
| Comparative | | | | |
| G | 0.117 | glucose | 0.058 | 65 |
| H | 0.117 | fructose | 0.058 | 22 |
| I | 0.117 | sucrose | 0.058 | 52 |
| J | — | sucrose | 0.175 | 30 |
| K | — | glucose | 0.175 | 22 |

The results confirm the superiority of maltose over sucrose or glucose, and demonstrate that sucrose, glucose and fructose at 0.058M inhibit plantlet production in the presence of maltose. However, addition of the sugar alcohols mannitol and sorbitol had no apparent effect on plantlet development.

EXAMPLES 10 to 13

Anthers of the barley cultivar Igri were cultured as previously described, except that agarose was replaced by 20% "Ficoll 400" (trade mark) (a synthetic polymer made by copolymerisation of sucrose and epichlorohydrin, ex. Pharmacia Ltd., Milton Keynes, U.K.) to produce a dense liquid medium on which anthers and embryos float, 5ml of the medium was removed every 48 hours and replaced by 5ml of fresh medium, and the only sugar in the medium was glucose at 0.0025, 0.005 or 0.01M (2.5, 5.0 or 10mM). In this way anthers were cultured on low glucose concentrations, which were maintained by regular addition of fresh medium. As a control, this procedure was also followed using medium containing 0.056M maltose, except that there was no removal of medium or addition of fresh medium.

Embryoids were obtained in these procedures showing that a maintained but low glucose concentration can support plant development from microspores of barley. After 4 weeks, all glucose containing media were replenished by removal of 5ml of medium and addition of 5ml of medium containing 0.056M maltose, to encourage plant development.

Results obtained are shown in Table III following:

TABLE III

| Example | Sugar | Sugar concentration (M) | Green plantlets per 100 anthers cultured |
|---|---|---|---|
| 10 | glucose | 0.0025 | 140 |
| 11 | glucose | 0.005 | 165 |
| 12 | glucose | 0.01 | 218 |
| 13 | maltose | 0.056 (not replenished) | 124 |

EXAMPLE 14

240 Anthers of the barley cultivar Igri were placed in 5ml of the callus induction medium of Foroughi-Wehr et al, Z. Pflanzenzuchtg. 77, 198–204 (1976) except for the presence of maltose at 0.175M in place of sucrose (not solidified with agarose). The anthers were ruptured by gentle mechanical pressure, thereby liberating microspores. The resulting suspension was filtered through a $50 \times 10^{-6}$m stainless steel sieve to remove large debris and was then centrifuged (65g, 650m/s$^2$) for 5 minutes. Supernatant fluid and floating debris were discarded and the solid residue (substantially isolated microspores) was resuspended in 1ml of the above medium.

Aliquots of 0.1ml of the resulting microspore suspension were cultured by the general procedure described above for anthers (i.e. by placing the aliquots on the surface of the 10ml of callus induction medium in 5cm Petri dishes) on medium containing 0.175M maltose.

1470 Green plantlets were obtained, representing a yield of 613 green plants per 100 anthers.

EXAMPLE 15

180 anthers (36 from each of 5 spikes) of the barley cultivar Igri were placed in 1 ml of the callus induction medium of Foroughi-Wehr et at modified by the exclusion of sucrose and agar and by the addition of 0.005M glutamine and 0.15M maltose. Microspores were isolated mechanically as described in example 14. After centrifugation the microspores were suspended in 3 ml of the same medium and incubated at 25° in a 25 ml conical flask on a rotary shaker (100 rpm). After 14 days the contents of the flask were spread over the surface of five 9cm petri dishes, each containing 30 ml of the same medium except that it was solidified with 0.8% Sea Plague agarose.

A total of 1095 green plants was obtained, representing a yield of 608 green plants per 100 anthers cultured.

EXAMPLE 16

Anthers of the barley cultivar Igri were cultured on the callus induction medium of Foroughi-Wehr et al, modified by the exclusion of sucrose and agar and by the inclusion of 0.005M glutamine, 20% Ficoll 400 and a trisaccharide at 0.15M. A comparison experiment was carried out in which the trisaccharide was replaced with 0.15M sucrose. The experiment was replicated 6 times. Each dish (containing 10 ml medium) received 12 anthers. The number of green plantlets per 100 anthers cultured was: maltotriose: 590; melezitoze: 392; and sucrose: 10.

EXAMPLE 17

The procedure described in Example 16 was carried out using the sugars trehalose and gentiobiose in accordance with the invention, and melibiose and turanose as comparison. The results, expressed as the number of green plantlets per 100 anthers cultured, illustrate the clear advantage of the use of sugars according to the invention: trehalose: 104; gentiobiose: 71; melibiose: 28; and turanose: 0.

EXAMPLE 18

The procedure described in Example 16 was carried out using dextrin (Dextrin precipitated by alcohol obtained from BDH) at 5% or maltose at 5% as the sugar.

The experiment was replicated 5 times. The number of green plantlets per 100 anthers cultured was dextrin 160; maltose 174.

EXAMPLE 19

Anthers of the barley cultivar Igri were cultured on the callus induction medium of Foroughi-Wehr, et al, modified by the exclusion of agar, by the addition of 0.005M glutamine and 20% Ficoll 400 and by the adjustment of the sucrose concentration to the values shown in Table IV (below). The experiment was replicated 15 times. For each replicate 36 anthers from each of 2 spikes were randomly assigned to the 6 treatments such that each dish (containing 10 ml medium) received 12 anthers. Results are shown in Table IV (below). Sucrose concentrations much lower than those used in prior processes gave high yields of green plants.

TABLE IV

| (M) Sucrose concentration | Green plantlets per 100 anthers cultured |
| --- | --- |
| 0.002 | 85 |
| 0.005 | 79 |
| 0.01 | 104 |
| 0.02 | 67 |
| 0.1 | 10 |

I claim:

1. A method of generating barley plants comprising culturing barley microspores on a sugar-containing medium and harvesting green plantlets from the medium characterized in that the sugar in the sugar-containing medium is selected from the group consisting of (a) glucose having a concentration in the medium of not greater than 0.03 mol/l; (b) oligosaccharides, containing 2 to 10 monosaccharide residues, at least two of which are glucose residues, having a concentration in the medium of 0.05 to 0.35 mol/l; or (c) polysaccharides, containing more than 10 monosaccharide residues, at least two of which are glucose residues, having a concentration in the medium of 2 to 12 percentage w/v (grams per 100 ml).

2. A method according to claim 1, wherein the oligosaccharides and polysaccharides contain exclusively glucose residues.

3. A method according to claim 1 wherein the oligosaccharides are disaccharides and trisaccharides.

4. A method according to claim 3 wherein the disaccharides are maltose, trehalose, cellobiose and gentiobiose.

5. A method according to claim 3, wherein the trisaccharides are maltotriose and melezitose.

6. A method according to claim 1, wherein the polysaccharides are dextrins.

7. A method according to any one of claims 1 to 6 wherein the concentration of glucose is not greater than 0.015 mol/l.

8. A method of generating barley seed comprising generating barley plants by a method according to any one of claims 1 to 6, cultivating green plantlets and deriving seed from resulting mature plants.